US009915390B2

(12) United States Patent
Kwan et al.

(10) Patent No.: US 9,915,390 B2
(45) Date of Patent: Mar. 13, 2018

(54) SELF-SINKING AERATION HOSE

(71) Applicants: Tak Kwong Kwan, Georgetown (CA); Hang Bi, Georgetown (CA)

(72) Inventors: Tak Kwong Kwan, Georgetown (CA); Hang Bi, Georgetown (CA)

( * ) Notice: Subject to any disclaimer, the term of this patent is extended or adjusted under 35 U.S.C. 154(b) by 0 days.

(21) Appl. No.: 15/375,018

(22) Filed: Dec. 9, 2016

(65) Prior Publication Data

US 2017/0122480 A1    May 4, 2017

Related U.S. Application Data

(63) Continuation-in-part of application No. 14/831,849, filed on Aug. 20, 2015, now Pat. No. 9,631,079.

(51) Int. Cl.
| | |
|---|---|
| *C08L 31/04* | (2006.01) |
| *C08L 27/06* | (2006.01) |
| *F16L 55/07* | (2006.01) |
| *A01K 63/04* | (2006.01) |
| *A01K 67/02* | (2006.01) |

(52) U.S. Cl.
CPC ............ *F16L 55/07* (2013.01); *A01K 63/042* (2013.01); *A01K 67/02* (2013.01); *C08L 27/06* (2013.01); *C08L 31/04* (2013.01); *C08L 2201/08* (2013.01); *C08L 2205/025* (2013.01); *C08L 2205/035* (2013.01); *C08L 2207/24* (2013.01)

(58) Field of Classification Search
None
See application file for complete search history.

(56) References Cited

U.S. PATENT DOCUMENTS

| | | | | |
|---|---|---|---|---|
| 3,951,894 | A * | 4/1976 | Whelan, Jr. | C08K 3/10 524/111 |
| 5,561,191 | A * | 10/1996 | Lundquist | C08F 8/00 252/400.31 |
| 6,140,380 | A * | 10/2000 | Mauk | C08J 9/06 516/11 |
| 2007/0176155 | A1* | 8/2007 | Granada, Jr. | C01F 5/14 252/601 |
| 2009/0308001 | A1* | 12/2009 | Wu | E04B 1/762 52/173.3 |

* cited by examiner

*Primary Examiner* — Peter A Salamon
(74) *Attorney, Agent, or Firm* — Richard D. Okimaw

(57) ABSTRACT

Disclosed herein is an aeration hose capable of diffusing bubbles of air within a body of water, comprising a) a hose portion derived from a composition, comprising a polyvinyl chloride resin; a first rubber component; a second rubber component; at least one copolymer; at least one low temperature plasticizer; at least one filler comprising copper dioxide; at least one heat stabilizer; at least one internal lubricant; at least one antioxidant; and at least one biofouling agent, wherein the hose portion comprises an outer hose portion, an inner hose portion and a plurality of hose apertures capable of receiving and diffusing pressurized air, wherein the hose is flexible and has no memory, and wherein the hose apertures are provided therethrough the inner hose portion and the outer hose portion and proportionally spaced about the outer hose portion along a length of the hose portion.

20 Claims, 4 Drawing Sheets

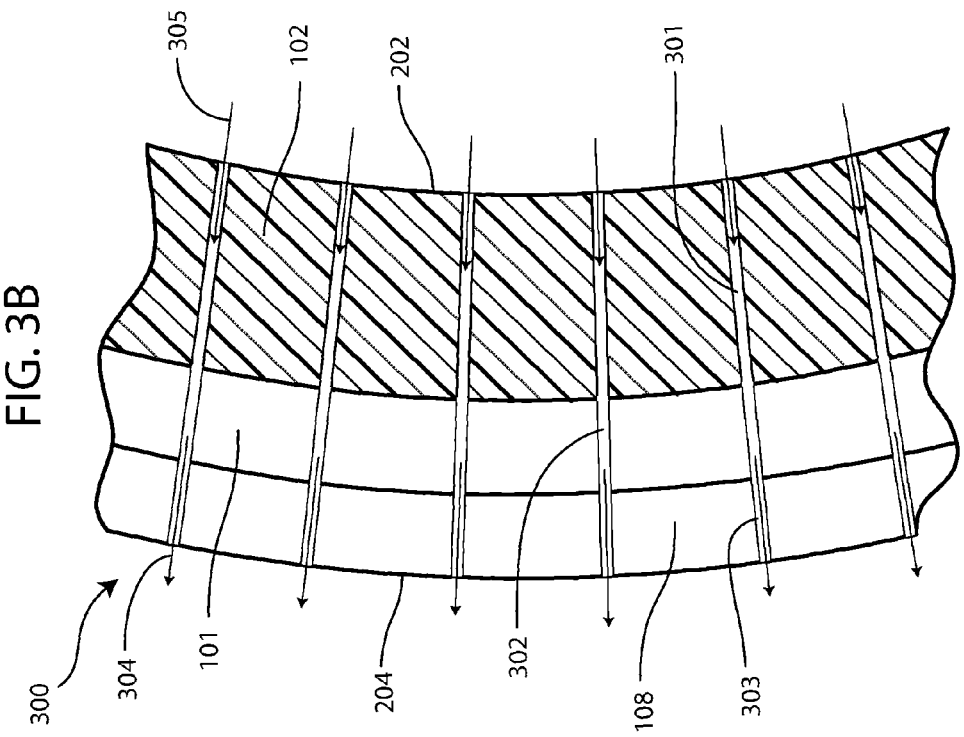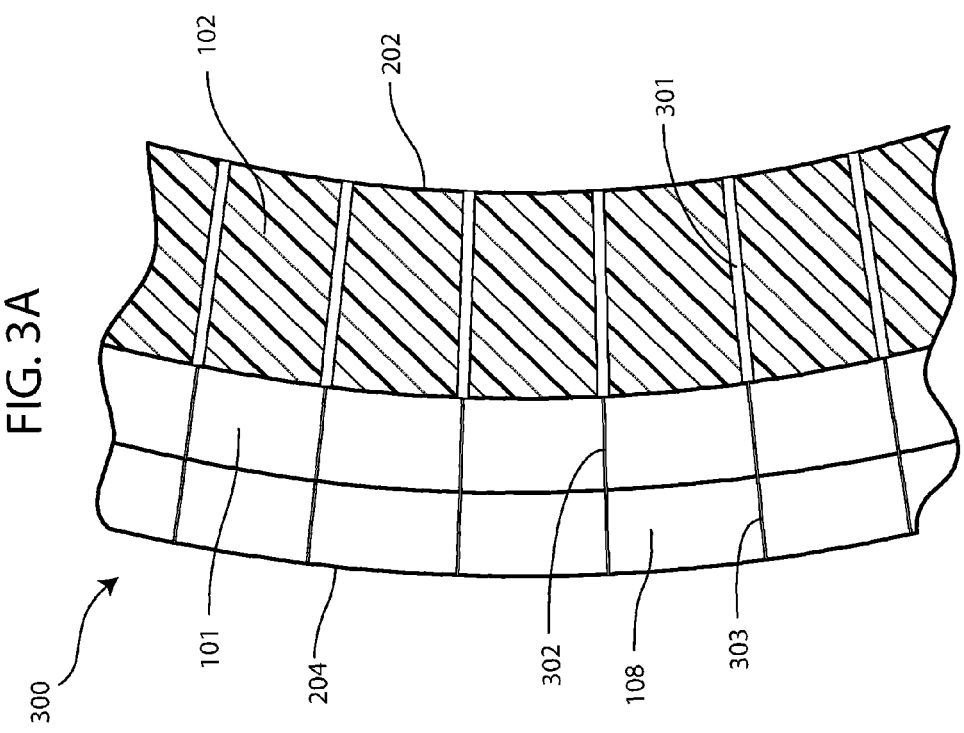

SELF-SINKING AERATION HOSE

CROSS REFERENCE TO RELATED APPLICATION

This application is a continuation-in-part of applicant's co-pending application Ser. No. 14/831,849, filed Aug. 20, 2015, the entire contents of which is hereby expressly incorporated by reference herein.

FIELD OF THE INVENTION

The present invention is in the field of aeration hoses capable of diffusing bubbles of air within a body of water. In particular, the disclosure pertains to PVC compositions useful with producing a self-sinking aeration hose that will diffuse air evenly along its entire length.

BACKGROUND OF THE DISCLOSURE

Aquatic pools, fishponds, sewage lagoons, wastewater treatment and/or fishing farms usually requires aeration devices to maintain the concentration of dissolved oxygen, which is necessary for aquatic underwater organisms and microorganisms, the stabilization of water quality, and the ecological balance of aquatic pools. Microorganisms require the absorption of dissolved oxygen from the water to decompose the redundant organic material and to perform nitrification and lower toxicities. The mixing of small air bubbles and water increases the concentration of dissolved oxygen of the pool water and promotes the decomposition rate of the organic materials by microorganisms.

Aeration systems and tubes can provide major increases in the oxygen concentration in a given water body. Current porous aeration tubes on the market today employ heavy loads that cause the tubes to sink to the bottom of an aquatic pool. There are additional disadvantages that include: weak aerobic capacity, easily clogged pores, and subsequently water that cannot easily be discharged.

Pollution and the preservation of water resources is a major global concern, but in some water body it is often difficult to provide aeration at the bottom and cumbersome and expensive installation methods greatly reduces the likelihood of widespread implementation. Therefore, in view of these limitations there is a need for improved aeration systems and tubing for oxygenation of a given water body.

SUMMARY OF THE INVENTION

In one aspect, disclosed herein is an aeration hose capable of diffusing bubbles of air within a body of water, comprising: a) a hose portion derived from a composition, comprising a polyvinyl chloride resin; a first rubber component; a second rubber component; at least one copolymer; at least one low temperature plasticizer; at least one filler comprising copper dioxide; at least one heat stabilizer; at least one internal lubricant; at least one antioxidant; and at least one biofouling agent, wherein the hose portion comprises an outer hose portion, an inner hose portion and a plurality of hose apertures capable of receiving and diffusing pressurized air, wherein the hose is flexible and has no memory, and wherein the hose apertures are provided therethrough the inner hose portion and the outer hose portion and proportionally spaced about the outer hose portion along a length of the hose portion; b) a first protective layer portion surrounding an outer diameter of the hose portion, comprising a plurality of first protective layer apertures provided therethrough an inner protective sheath diameter and an outer protective sheath diameter and spaced along a length of the protective sheath, wherein the first protective layer is flexible and has memory; and c) a second protective layer portion surrounding an outer diameter of the first protective layer portion, comprising a plurality of second protective layer apertures provided therethrough an inner second protective layer diameter and an outer second protective layer diameter and spaced along a length of the second protective layer, wherein the second protective layer is flexible and has memory, wherein the second protective layer apertures are capable of providing communication for the air to flow to a body of water from the corresponding first protective layer apertures, and wherein the hose apertures are capable of providing communication for the air to flow from the inner hose portion to a plurality of corresponding first protective layer apertures.

In another aspect, disclosed herein is a method of aerating and/or deicing a body of water with an aeration hose capable of diffusing bubbles of air within a body of water, comprising: a) a hose portion derived from a composition, comprising a polyvinyl chloride resin; a first rubber component; a second rubber component; at least one copolymer; at least one low temperature plasticizer; at least one filler comprising calcium carbonate; at least one heat stabilizer; at least one internal lubricant; at least one antioxidant; and at least one biofouling agent, wherein the hose portion comprises an outer hose portion, an inner hose portion and a plurality of hose apertures capable of receiving and diffusing pressurized air, wherein the hose is flexible and has no memory, and wherein the hose apertures are provided therethrough the inner hose portion and the outer hose portion and proportionally spaced about the outer hose portion along a length of the hose portion; b) a first protective layer portion surrounding an outer diameter of the hose portion, comprising a plurality of first protective layer apertures provided therethrough an inner protective sheath diameter and an outer protective sheath diameter and spaced along a length of the protective sheath, wherein the first protective layer is flexible and has memory; and c) a second protective layer portion surrounding an outer diameter of the first protective layer portion, comprising a plurality of second protective layer apertures provided therethrough an inner second protective layer diameter and an outer second protective layer diameter and spaced along a length of the second protective layer, wherein the second protective layer is flexible and has memory, wherein the second protective layer apertures are capable of providing communication for the air to flow to a body of water from the corresponding first protective layer apertures, and wherein the hose apertures are capable of providing communication for the air to flow from the inner hose portion to a plurality of corresponding first protective layer apertures.

BRIEF DESCRIPTION OF THE DRAWINGS

FIG. 3A is an illustration of a cutaway view of an aeration hose 300 comprising a plurality of hose apertures 301, wherein the first protective layer apertures 302 and the second protective layer apertures 303 are closed.

FIG. 3B is an illustration of a cutaway view of an aeration hose 300 comprising a plurality of hose apertures 301, wherein the first protective layer apertures 302 and the second protective layer apertures 303 are open.

DETAILED DESCRIPTION OF THE EMBODIMENTS

The following is a detailed description of certain specific embodiments of the self-sinking aeration hose disclosed herein.

INTRODUCTION

In one aspect, disclosed herein is an aeration hose capable of diffusing bubbles of air within a body of water, comprising: a) a hose portion derived from a composition, comprising a polyvinyl chloride resin; a first rubber component; a second rubber component; at least one copolymer; at least one low temperature plasticizer; at least one filler comprising copper dioxide; at least one heat stabilizer; at least one internal lubricant; at least one antioxidant; and at least one biofouling agent, wherein the hose portion comprises an outer hose portion, an inner hose portion and a plurality of hose apertures capable of receiving and diffusing pressurized air, and wherein the hose is flexible and has no memory, wherein the hose apertures are provided therethrough the inner hose portion and the outer hose portion and proportionally spaced about the outer hose portion along a length of the hose portion; b) a first protective layer portion surrounding an outer diameter of the hose portion, comprising a plurality of first protective layer apertures provided therethrough an inner protective sheath diameter and an outer protective sheath diameter and spaced along a length of the protective sheath, wherein the first protective layer is flexible and has memory; and c) a second protective layer portion surrounding an outer diameter of the first protective layer portion, comprising a plurality of second protective layer apertures provided therethrough an inner second protective layer diameter and an outer second protective layer diameter and spaced along a length of the second protective layer, wherein the second protective layer is flexible and has memory, wherein the second protective layer apertures are capable of providing communication for the air to flow to a body of water from the corresponding first protective layer apertures, wherein the hose apertures are capable of providing communication for the air to flow from the inner hose portion to a plurality of corresponding first protective layer apertures, and wherein the hose apertures are comprised of between about 20 to 500 apertures per square inch of the hose portion.

Figure 1:
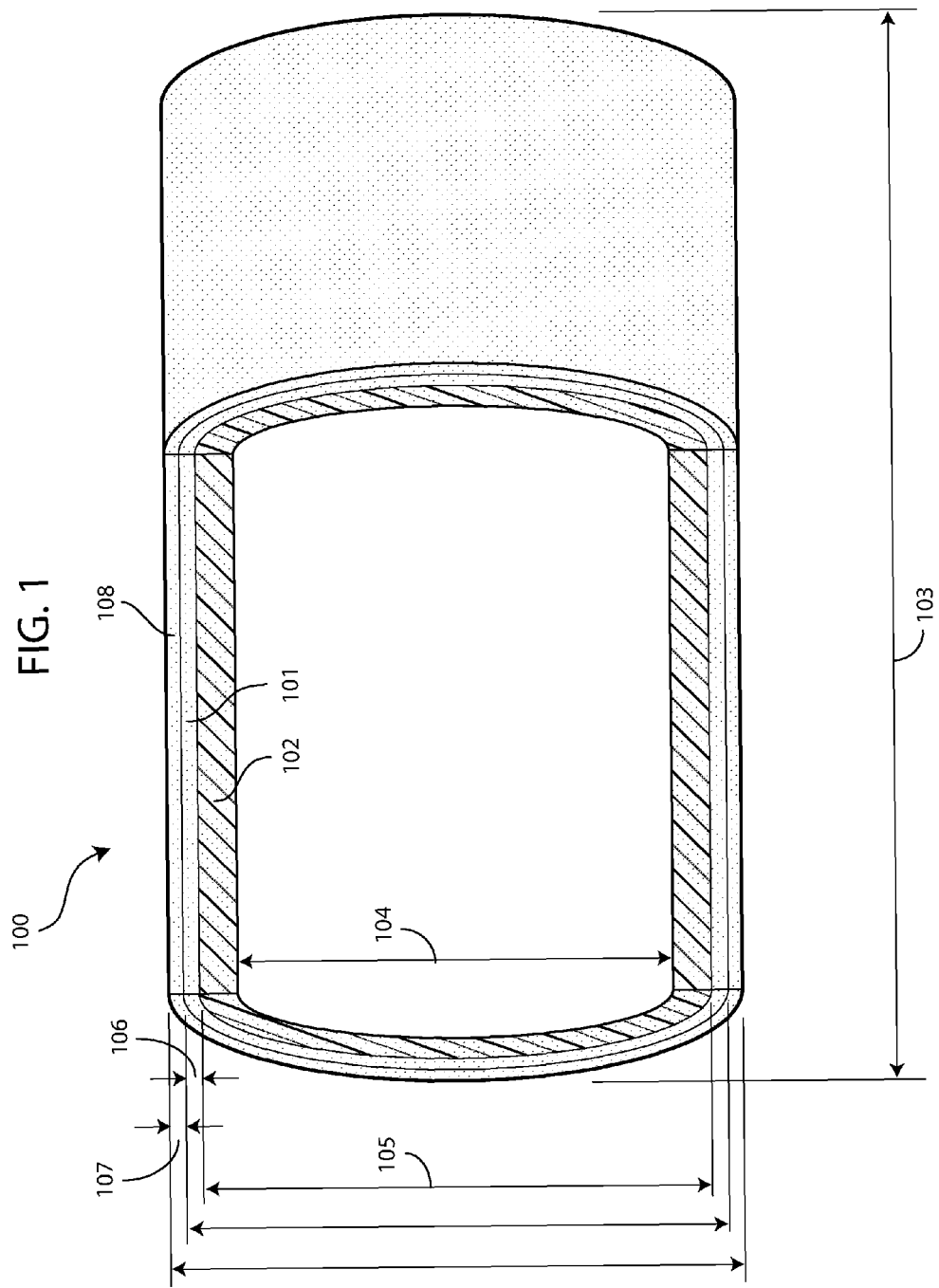
FIG. 1 is an illustration of a cutaway side view of an aeration hose 100 comprising an inner hose diameter 104, an outer hose diameter 105 and aeration hose length 103.

Referring to the drawings, FIG. 1 illustrates an aeration hose 100 comprising a hose portion 102 with an inner hose diameter 104, an outer hose diameter 105 and aeration hose length 103. The aeration hose 100 comprises a first protective layer portion 101 and a second protective layer portion 108 with a first protective layer thickness 106 and a second protective layer thickness 107, respectively. In some embodiments, the first protective layer is comprised of tear resist polyurethane with a thickness of between about 0.1 mm to 5 mm. In some embodiments, the second protective layer is comprised of heat resist silicone rubber with a thickness of between about 0.1 mm to 5 mm. In some embodiments, the second protective layer is comprised of heat resist silicone rubber with a thickness of between about 0.1 mm to 5 mm. In some embodiments, the heat resist silicone rubber layer can withstand temperatures ranging from minus 40° C. to 160° C.

In some embodiments, the aeration hose length 103 is between about 1 m and 6000 m. In some embodiments, the hose portion has an inner diameter of between about 0.1 inches and 3 inches and an outer diameter of between about 0.23 inches and 5 inches. In some embodiments, the hose portion has an inner diameter of about 0.38 inches, 0.5 inches, 0.63 inches, 0.75 inches or 1.0 inch. In some embodiments, the hose portion has an outer diameter of about 0.69 inches, 0.96 inches, 1.065 inches, 1.275 inches or 1.69 inches.

Figure 2:
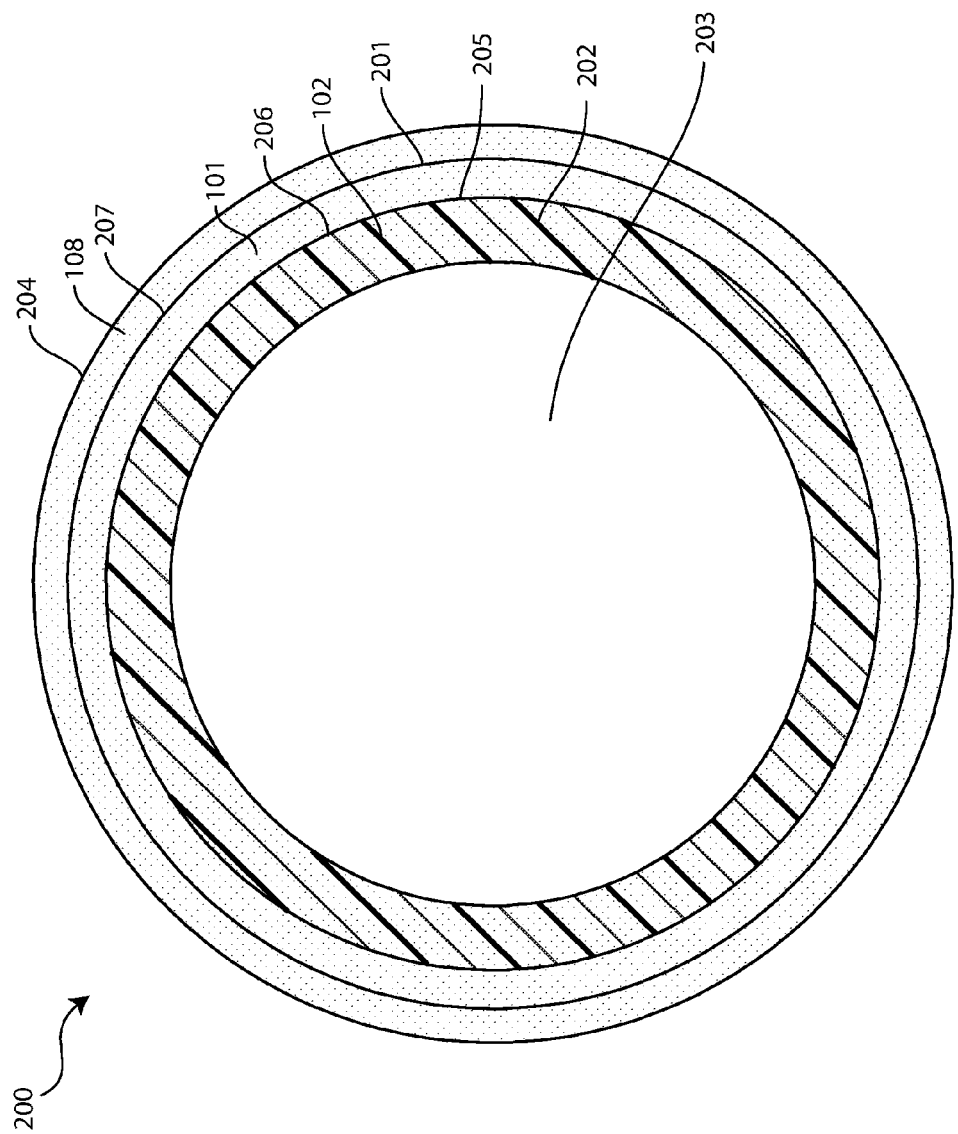
FIG. 2 is an illustration of a cutaway view of an aeration hose 200 comprising an inner hose portion 203, an outer hose portion 205 and a second protective layer outer surface 204.

FIG. 2 is an illustration of a cutaway view of an aeration hose 200 comprising an inner hose volume 203, an inner hose surface 202, an outer hose surface 205 The second protective layer 108 comprises a second protective layer outer surface 204 and a second protective layer inner surface 207. The first protective layer 101 comprises a first protective layer outer surface 201 and a first protective layer inner surface 206. In some embodiments, the first protective layer is comprised of polyurethane, silicon, EPDM (ethylene propylene diene monomer), thermoplastic rubber or natural rubber. In some embodiments, the second protective layer is comprised of silicone rubber, silicon, EPDM (ethylene propylene diene monomer), thermoplastic rubber or natural rubber. In some embodiments, the first protective layer is bonded to the outer surface of the hose portion along length of the hose portion. In some embodiments, the hose portion, the first protective layer, second protective layer are bonded along the length of the aeration hose via a co-extrusion of the composition or component of each.

FIGS. 3A and 3B are illustrations of a cutaway view of an aeration hose 300 comprising a hose portion 102 with a plurality of hose apertures 301, a first protective layer 101 with a plurality of first protective layer apertures 302 and a second protective layer 108 with a plurality of second protective layer apertures 303. In some embodiments, the first protective layer and/or the second protective layer return to their original shape "memory" and the first protective layer apertures and/or the second protective layer apertures close when air is not flowing via the hose apertures. The aeration hose 300 of FIG. 3A depicts the first protective layer apertures 302 and the second protective layer apertures 303 in a closed position. In contrast, the inner air flow 305 of the aeration hose 300 travels through the hose apertures 301 resulting in the first protective layer apertures 302 and the second protective layer apertures 303 being in the open position with the exiting air flow 304. In this aspect, the first protective layer and the second protective layer have no memory and with the lack of air pressure the first protective layer apertures 302 and the second protective layer apertures 303 are capable of closing preventing debris from entering the aeration hose disclosed herein. As such, the ability for the first protective layer apertures 302 and the second protective layer apertures 303 to close when air flow is off results in reduced failure due to debris entering the aeration hose disclosed herein. In some embodiments, the first protective layer apertures are comprised of between about 20 to 500 apertures per square inch of the first protective layer. In some embodiments, the second protective layer apertures are comprised of between about 20 to 500 apertures per square inch of the second protective layer. In some embodiments, the hose apertures, first protective layer apertures and second protective layer apertures each independently have an aperture diameter of between about 0.05 mm and 3 mm. In some embodiments, the hose apertures, first protective layer apertures and second protective layer apertures each independently have an aperture diameter of between about 0.2 mm and 1.0 mm. In some embodiments, the hose apertures, first protective layer apertures and second protective layer apertures are formed via plunging therethrough the aeration hose with one or more 0.1 mm to 4 mm needles. In some embodiments, the hose apertures, first protective layer apertures and second protective layer apertures are formed via plunging therethrough the aeration hose with one or more 0.1 mm to 1.5 mm needles.

In some embodiments, the aeration hose is comprised of negative buoyancy plastic. In some embodiments, the hose portion is comprised of negative buoyancy plastic. In some embodiments, the aeration hose is comprised of negative buoyancy plastic, and wherein the aeration hose is deployed the bottom of the body of water without weights. In some embodiments, the hose portion is comprised of negative buoyancy plastic, and wherein the aeration hose is deployed the bottom of the body of water without weights.

Figure 4:
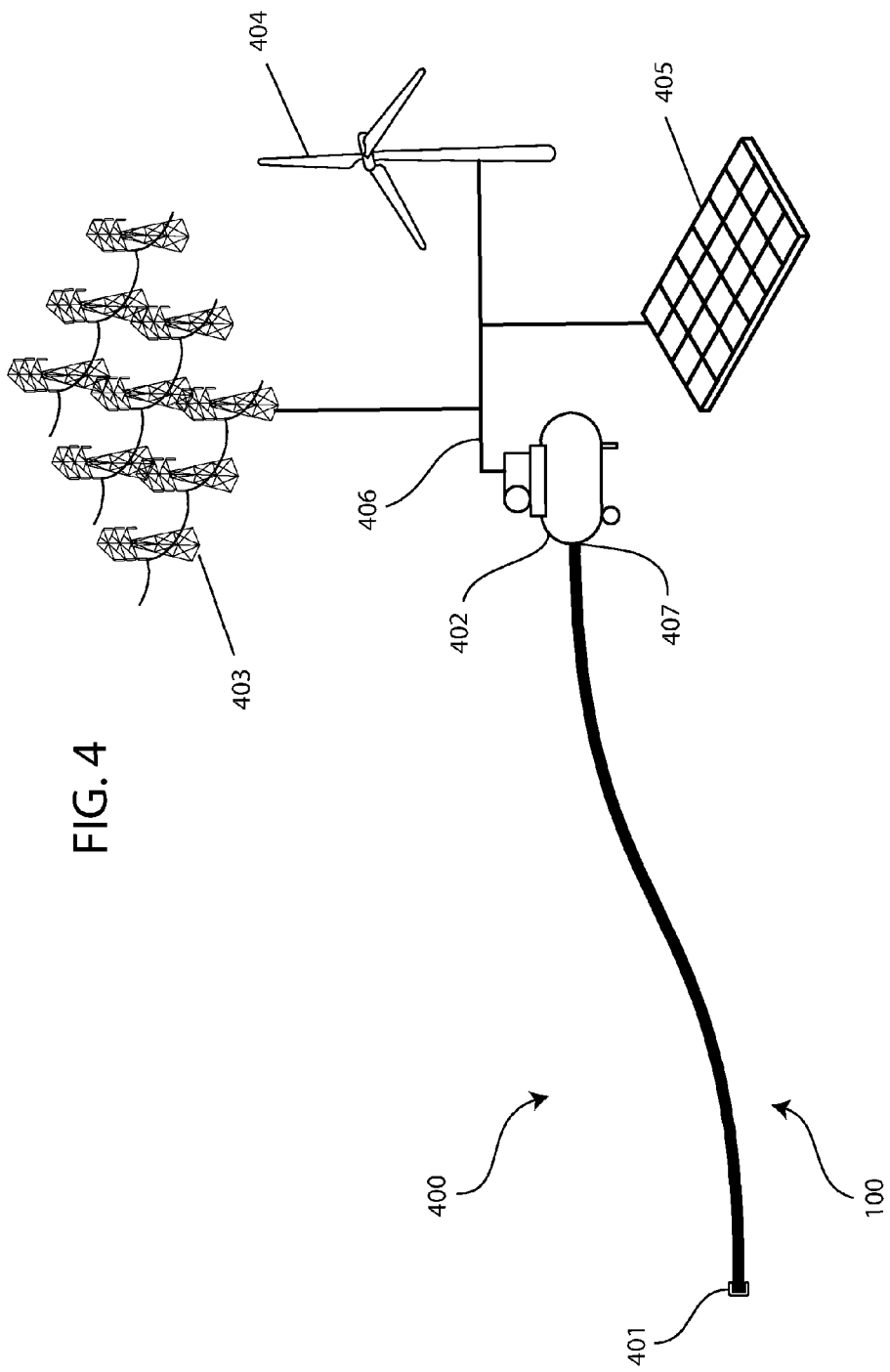
FIG. 4 is an illustration of an aeration hose 100 comprising a closed end 401 and an air pump or compressor 402 connected an open end 407.

Turning to FIG. 4, the aeration hose 100 comprising a closed end 401 and an air pump or compressor 402 connected an open end 407. In some embodiments, the aeration hose disclosed herein are designed for even distribution of air bubbles along the length of the aeration hose. In some embodiments, the aeration hose disclosed herein is capable of operating in conjunction with a land installation of an air pump or compressor 402 with between 25 Watts and 500 Watts. In some embodiments, the aeration hose disclosed herein is capable of operating in conjunction with a land installation of a 75 Watt air pump or compressor 402 capable of supplying air pressure to 1000 M of aeration hose. The air pump or compressor 402 is in electrical communication via one or more power wires 406 with a power source. In some embodiments, the power source is selected from the group consisting of a municipal electrical power grid, one or more generators, street lamp, a battery, and a transformer 403. In some embodiments, the air pump or compressor 402 of the aeration hose 100 is powered by electricity provided by one or more solar panels 405 or one or more wind turbines or windmills 404. In some embodiments, the minimum pressure used with the aeration hose is between about 5 psi and 3 bar. In some embodiments, the maximum pressure used with the aeration hose is between about 25 psi and 6 bar. In some embodiments, the airflow with the aeration hose is between about 0.01 cfm/ft and 80 lpm/m.

An Example of Aeration Hose Air Pressure Specifications:

| | |
|---|---|
| Minimum pressure: | 20 psi-1.4 bar. |
| Maximum pressure: | ½" I.D. and ¾" I.D.: 50 psi-3.4 bar. |
| | 1" I.D.: 70 psi-4.8 bar. |
| Suggested airflow: | ½" I.D.: 0.05 cfm/ft-4.62 lpm/m. |
| | ¾" I.D.: 0.065 cfm/ft-6.04 lpm/m. |
| | 1" I.D.: 0.1 cfm/ft -9.28 lpm/m. |
| Maximum airflow: | ½" I.D.: 0.1 cfm/ft-9.28 lpm/m. |
| | ¾" I.D.: 0.12 cfm/ft-11.2 lpm/m. |
| | 1" I.D.: 0.2 cfm/ft-18.56 lpm/m. |

In some embodiments, the hose portion is capable of diffusing bubbles of air in a body of water that is at a temperature between about −10° C. and 70° C.

In some embodiments, the hose portion is capable of diffusing bubbles of air in a body of water that is at a temperature between about −4° C. and 65° C.

In some embodiments, the second protective layer is comprised of heat resist silicone rubber is capable of diffusing bubbles of air in a body of water that is at a temperature between about −40° C. and 160° C.

In some embodiments, the polyvinyl chloride resin comprises a PVC/VA (polyvinyl chloride/polyvinyl acetate copolymer) with an inherent viscosity of between about 0.5 to 0.9 and a K-value of between about 56 to 64.

In some embodiments, the first rubber component is present in an amount between about 5 to 25 parts per hundred parts of resin.

In some embodiments, the second rubber component is present in an amount between about 55 to 75 parts per hundred parts of resin.

In some embodiments, the copolymer comprises at least one ethylene copolymer.

In some embodiments, the low temperature plasticizer comprises di-octyl adipate, Tris-2-Ethylhexyl-Trimellitate or combinations thereof.

In some embodiments, the copper dioxide is present in an amount between about 40 to 170 parts per hundred parts of resin.

In some embodiments, the polyvinyl chloride resin comprises a PVC/VA with an inherent viscosity of between about 0.7 to 0.8 and a K-value of between about 59 to 62.

In some embodiments, the first rubber component comprises an amount of NBR between about 10 to 20 parts per hundred parts of resin.

In some embodiments, the second rubber component comprises an amount of 15 to 115 mesh crumbed tire between about 55 to 75 parts per hundred parts of resin.

In some embodiments, the copolymer comprises an amount of ethylene-vinyl acetate between about 10 to 40 parts per hundred parts of resin.

In some embodiments, the low temperature plasticizer comprises an amount of di-octyl adipate between about 45 to 55 parts per hundred parts of resin, an amount of Tris-2-Ethylhexyl-Trimellitate between about 45 to 55 parts per hundred parts of resin or a combinations thereof.

In some embodiments, the copper dioxide is present in an amount between about 60 to 155 parts per hundred parts of resin.

In some embodiments, the at least one heat stabilizer comprising an amount of calcium stearate between about 1 to 4 parts per hundred parts of resin, an amount of zinc stearate between about 1 to 4 parts per hundred parts of resin or a combinations thereof.

In some embodiments, the at least one internal lubricant is present in an amount between about 0.01 to 0.05 parts per hundred parts of resin.

In some embodiments, the at least one antioxidant is present in an amount between about 0.005 to 0.075 parts per hundred parts of resin.

In some embodiments, the at least one biofouling agent is selected from the group consisting of glycine betaine, sulfobetaine, titanium dioxide nanotubes or combinations thereof.

In some embodiments, the hose portion as disclosed herein comprises a) the polyvinyl chloride resin comprises a PVC/VA with an inherent viscosity of between about 0.7 to 0.8 and a K-value of between about 59 to 62; b) the first rubber component comprises an amount of NBR between about 12 to 18 parts per hundred parts of resin; c) the second rubber component comprises an amount of 20 to 110 mesh crumbed tire between about 60 to 70 parts per hundred parts of resin; d) the copolymer comprises an amount of ethylene-vinyl acetate between about 15 to 35 parts per hundred parts of resin; e) the low temperature plasticizer comprises an amount of di-octyl adipate between about 45 to 55 parts per hundred parts of resin, an amount of Tris-2-Ethylhexyl-Trimellitate between about 45 to 55 parts per hundred parts of resin or a combination thereof; d) the copper dioxide is present in an amount between about 60 to 155 parts per hundred parts of resin; e) the at least one heat stabilizer comprising an amount of calcium stearate between about 1 to 4 parts per hundred parts of resin, an amount of zinc stearate between about 1 to 4 parts per hundred parts of resin or a combination thereof; f) the at least one internal lubricant is present in an amount between about 0.01 to 0.05 parts per hundred parts of resin; and g) the at least one antioxidant is present in an amount between about 0.005 to 0.075 parts per hundred parts of resin, wherein the at least one biofouling agent is selected from an amount of glycine betaine between about 0.02 to 0.03 parts per hundred parts of resin, an amount of sulfobetaine between about 0.02 to 0.03 parts per hundred parts of resin, an amount of titanium dioxide nanotubes between about 0.04 to 0.06 parts per hundred parts of resin or combinations thereof.

In some embodiments, the hose portion as disclosed herein comprises a) the polyvinyl chloride resin comprises a PVC/VA with an inherent viscosity of between about 0.7 to 0.8 and a K-value of between about 59 to 62; b) the first rubber component comprises an amount of NBR between about 12 to 18 parts per hundred parts of resin; c) the second rubber component comprises an amount of 20 to 110 mesh crumbed tire between about 60 to 70 parts per hundred parts of resin; d) the copolymer comprises an amount of ethylene-vinyl acetate between about 15 to 35 parts per hundred parts of resin; e) the low temperature plasticizer comprises an amount of di-octyl adipate between about 45 to 55 parts per hundred parts of resin, an amount of Tris-2-Ethylhexyl-Trimellitate parts per hundred parts of resin or a combination thereof; e) the copper dioxide is present in an amount of about 116.16 parts per hundred parts of resin, 83.87 parts per hundred parts of resin, 128 parts per hundred parts of resin, 130.3 parts per hundred parts of resin or 132.44 parts per hundred parts of resin; f) the at least one heat stabilizer comprising an amount of calcium stearate between about 1 to 4 parts per hundred parts of resin, an amount of zinc stearate between about 1 to 4 parts per hundred parts of resin or a combination thereof; g) the at least one internal lubricant is present in an amount between about 0.01 to 0.05 parts per hundred parts of resin; and h) the at least one antioxidant is present in an amount between about 0.005 to 0.075 parts per hundred parts of resin, wherein the at least one biofouling agent is selected from an amount of glycine betaine between about 0.02 to 0.03 parts per hundred parts of resin, an amount of sulfobetaine between about 0.02 to 0.03 parts per hundred parts of resin, an amount of titanium dioxide nanotubes between about 0.04 to 0.06 parts per hundred parts of resin or combinations thereof.

In some embodiments, the hose portion as disclosed herein comprises a) the polyvinyl chloride resin comprises PVC/VA (polyvinylchloride/polyvinyl acetate copolymer) with an inherent viscosity of about 0.787, and a K-value of about 60.9 the first rubber component comprises an amount of NBR of about 15 parts per hundred parts of resin; b) the second rubber component comprises an amount of 20 to 110 mesh crumbed tire of about 65 parts per hundred parts of resin; c) the copolymer comprises an amount of ethylene-vinyl acetate of about 25 parts per hundred parts of resin; d) the low temperature plasticizer comprises an amount of di-octyl adipate of about 50 parts per hundred parts of resin and an amount of Tris-2-Ethylhexyl-Trimellitate of about 50 parts per hundred parts of resin; e) the copper dioxide is present in an amount of about 116.16 parts per hundred parts of resin, 83.87 parts per hundred parts of resin, 128 parts per hundred parts of resin, 130.3 parts per hundred parts of resin or 132.44 parts per hundred parts of resin; f) the at least one heat stabilizer comprises an amount of calcium stearate of about 3 parts per hundred parts of resin and an amount of zinc stearate of about 3 parts per hundred parts of resin; g) the at least one internal lubricant comprises an amount of stearic acid of about 0.03 parts per hundred parts of resin; h) the at least one antioxidant comprises an amount of ADK STAB AO-50 (Octadecyl 3-(3,5-di-tert-butyl-4-hydroxyphenyl)propionate) of about 0.025 parts per hundred parts of resin; and wherein the at least one biofouling agent comprises an amount of glycine betaine of about 0.025 parts per hundred parts of resin, an amount of sulfobetaine of about 0.025 parts per hundred parts of resin and an amount of titanium dioxide nanotubes of about 0.05 parts per hundred parts of resin.

In another aspect, disclosed herein are compositions comprising: a polyvinyl chloride resin; a first rubber component; a second rubber component; at least one copolymer; at least one low temperature plasticizer; at least one filler comprising copper dioxide; at least one heat stabilizer; at least one internal lubricant; at least one antioxidant; and at least one biofouling agent.

In some embodiments, the polyvinyl chloride resin comprises a PVC/VA (polyvinyl chloride/polyvinyl acetate copolymer) with an inherent viscosity of between about 0.5 to 0.9 and a K-value of between about 56 to 64.

In some embodiments, the first rubber component is present in an amount between about 5 to 25 parts per hundred parts of resin.

In some embodiments, the second rubber component is present in an amount between about 55 to 75 parts per hundred parts of resin.

In some embodiments, the copolymer comprises at least one ethylene copolymer.

In some embodiments, the low temperature plasticizer comprises di-octyl adipate, Tris-2-Ethylhexyl-Trimellitate or combinations thereof.

In some embodiments, the copper dioxide is present in an amount between about 40 to 170 parts per hundred parts of resin.

In some embodiments, the polyvinyl chloride resin comprises a PVC/VA with an inherent viscosity of between about 0.7 to 0.8 and a K-value of between about 59 to 62.

In some embodiments, the first rubber component comprises an amount of NBR between about 10 to 20 parts per hundred parts of resin.

In some embodiments, the second rubber component comprises an amount of 15 to 115 mesh crumbed tire between about 55 to 75 parts per hundred parts of resin.

In some embodiments, the copolymer comprises an amount of ethylene-vinyl acetate between about 10 to 40 parts per hundred parts of resin.

In some embodiments, the low temperature plasticizer comprises an amount of di-octyl adipate between about 45 to 55 parts per hundred parts of resin, an amount of Tris-2-Ethylhexyl-Trimellitate between about 45 to 55 parts per hundred parts of resin or a combinations thereof.

In some embodiments, the copper dioxide is present in an amount between about 60 to 155 parts per hundred parts of resin.

In some embodiments, the at least one heat stabilizer comprising an amount of calcium stearate between about 1 to 4 parts per hundred parts of resin, an amount of zinc stearate between about 1 to 4 parts per hundred parts of resin or a combinations thereof.

In some embodiments, the at least one internal lubricant is present in an amount between about 0.01 to 0.05 parts per hundred parts of resin.

In some embodiments, the at least one antioxidant is present in an amount between about 0.005 to 0.075 parts per hundred parts of resin.

In some embodiments, the at least one biofouling agent is selected from the group consisting of glycine betaine, sulfobetaine, titanium dioxide nanotubes or combinations thereof.

In some embodiments, the composition comprises a) the polyvinyl chloride resin comprises a PVC/VA with an inherent viscosity of between about 0.7 to 0.8 and a K-value of between about 59 to 62; b) the first rubber component comprises an amount of NBR between about 12 to 18 parts per hundred parts of resin; c) the second rubber component comprises an amount of 20 to 110 mesh crumbed tire between about 60 to 70 parts per hundred parts of resin; d) the copolymer comprises an amount of ethylene-vinyl acetate between about 15 to 35 parts per hundred parts of resin; e) the low temperature plasticizer comprises an amount of di-octyl adipate between about 45 to 55 parts per hundred parts of resin, an amount of Tris-2-Ethylhexyl-Trimellitate between about 45 to 55 parts per hundred parts of resin or a combination thereof; d) the copper dioxide is present in an amount between about 60 to 155 parts per hundred parts of resin; e) the at least one heat stabilizer comprising an amount of calcium stearate between about 1 to 4 parts per hundred parts of resin, an amount of zinc stearate between about 1 to 4 parts per hundred parts of resin or a combination thereof; f) the at least one internal lubricant is present in an amount between about 0.01 to 0.05 parts per hundred parts of resin; and g) the at least one antioxidant is present in an amount between about 0.005 to 0.075 parts per hundred parts of resin, wherein the at least one biofouling agent is selected from an amount of glycine betaine between about 0.02 to 0.03 parts per hundred parts of resin, an amount of sulfobetaine between about 0.02 to 0.03 parts per hundred parts of resin, an amount of titanium dioxide nanotubes between about 0.04 to 0.06 parts per hundred parts of resin or combinations thereof.

In some embodiments, the composition comprises a) the polyvinyl chloride resin comprises a PVC/VA with an inherent viscosity of between about 0.7 to 0.8 and a K-value of between about 59 to 62; b) the first rubber component comprises an amount of NBR between about 12 to 18 parts per hundred parts of resin; c) the second rubber component comprises an amount of 20 to 110 mesh crumbed tire between about 60 to 70 parts per hundred parts of resin; d) the copolymer comprises an amount of ethylene-vinyl acetate between about 15 to 35 parts per hundred parts of resin; e) the low temperature plasticizer comprises an amount of di-octyl adipate between about 45 to 55 parts per hundred parts of resin, an amount of Tris-2-Ethylhexyl-Trimellitate parts per hundred parts of resin or a combination thereof; e) the copper dioxide is present in an amount of about 116.16 parts per hundred parts of resin, 83.87 parts per hundred parts of resin, 128 parts per hundred parts of resin, 130.3 parts per hundred parts of resin or 132.44 parts per hundred parts of resin; f) the at least one heat stabilizer comprising an amount of calcium stearate between about 1 to 4 parts per hundred parts of resin, an amount of zinc stearate between about 1 to 4 parts per hundred parts of resin or a combination thereof; g) the at least one internal lubricant is present in an amount between about 0.01 to 0.05 parts per hundred parts of resin; and h) the at least one antioxidant is present in an amount between about 0.005 to 0.075 parts per hundred parts of resin, wherein the at least one biofouling agent is selected from an amount of glycine betaine between about 0.02 to 0.03 parts per hundred parts of resin, an amount of sulfobetaine between about 0.02 to 0.03 parts per hundred parts of resin, an amount of titanium dioxide nanotubes between about 0.04 to 0.06 parts per hundred parts of resin or combinations thereof.

In some embodiments, the composition comprises a) the polyvinyl chloride resin comprises PVC/VA (polyvinylchloride/polyvinyl acetate copolymer) with an inherent viscosity of about 0.787, and a K-value of about 60.9 the first rubber component comprises an amount of NBR of about 15 parts per hundred parts of resin; b) the second rubber component comprises an amount of 20 to 110 mesh crumbed tire of about 65 parts per hundred parts of resin; c) the copolymer comprises an amount of ethylene-vinyl acetate of about 25 parts per hundred parts of resin; d) the low temperature plasticizer comprises an amount of di-octyl adipate of about 50 parts per hundred parts of resin and an amount of Tris-2-Ethylhexyl-Trimellitate of about 50 parts per hundred parts of resin; e) the copper dioxide is present in an amount of about 116.16 parts per hundred parts of resin, 83.87 parts per hundred parts of resin, 128 parts per hundred parts of resin, 130.3 parts per hundred parts of resin or 132.44 parts per hundred parts of resin; f) the at least one heat stabilizer comprises an amount of calcium stearate of about 3 parts per hundred parts of resin and an amount of zinc stearate of about 3 parts per hundred parts of resin; g) the at least one internal lubricant comprises an amount of stearic acid of about 0.03 parts per hundred parts of resin; h) the at least one antioxidant comprises an amount of ADK STAB AO-50 (Octadecyl 3-(3,5-di-tert-butyl-4-hydroxyphenyl)propionate) of about 0.025 parts per hundred parts of resin; and wherein the at least one biofouling agent comprises an amount of glycine betaine of about 0.025 parts per hundred parts of resin, an amount of sulfobetaine of about 0.025 parts per hundred parts of resin and an amount of titanium dioxide nanotubes of about 0.05 parts per hundred parts of resin.

Polyvinylchloride

PVC (Polyvinyl chloride) resin has a combination of properties which make it particularly suitable for use as a structural material. In applications in which impact strength of the structural plastic is important, the PVC can be formulated with impact-modifier resins which improve the impact strength of the resulting composition. Such high impact-strength PVC compositions can be readily extruded or otherwise formed into a variety of articles which have excellent impact strength, toughness and other desired mechanical and chemical properties.

The PVC constituent can comprise a mixture of a homopolymer and one or more copolymers of vinyl chloride and/or chlorinated PVC or a mixture of two or more copolymers of vinyl chloride and/or chlorinated PVC. In the disclosure herein, the PVC component can be copolymer of vinyl chloride and one or more other monomers, for example, VA (vinyl acetate) and the like, vinylidene halides such as vinylidene chloride, alkyl esters of carboxylic acids such as acrylic acid, ethyl acrylate, 2-ethylhexyl acrylate and the like, unsaturated hydrocarbons such as ethylene, propylene, isobutylene and the like, allyl compounds such as allyl acetate and the like. In the use of a copolymer of vinyl chloride, it is preferred that the vinyl chloride content comprise at least about 80 wt % of the copolymer. In some embodiments, the PVC constituent of the composition of the present invention comprises a copolymer of vinyl chloride with VA, particularly a copolymer having a K-value of from about 56 to 64, most preferably from about 59 to 62.

Stabilizers for PVC

Polymers and copolymers of PVC and vinyl acetate can be sensitive to heat. For this reason, heat stabilizers are usually added to prevent the polymers from decomposing during normal processing.

The term "stabilizer" as used herein shall mean one or more organic or inorganic compounds useful for protection of PVC against thermal, ultraviolet light, and/or mechanical degradation. The stabilizer may enhance the effect of the stabilizer system for the PVC and/or act as an antioxidant or stabilizer for the NBR rubber as well. Examples of conventional stabilizers are disclosed in the Kirk-Othmer Encyclopedia of Chemical Technology, "Heat Stabilizers", vol 12, pages 1071-91 (John Wiley, N Y 1994), incorporated herein by reference, and is not intended to be limiting to the disclosure herein.

Stabilizers may include organotin compounds such as alkyltin, dialkyltin, aryltin, poly(dialkyltin maleate), dialkyltin bis(alkyl maleate), dialkyltin bis(2-alkylthioglycolate), where the alkyl group is $C_4$-$C_8$. Some stabilizers contain calcium, zinc, magnesium, lead, barium and cadmium salts or soaps. In some embodiments, the stabilizer is comprised of combinations of Ca—Zn, Ba—Ca—Zn and Ba—Zn. Moreover, mixtures of alkaline earth metal salts and polyhydric alcohols. Combinations of aluminum salts and calcium salts may also be used as stabilizer components.

Additional stabilizer components may include epoxy compounds, antioxidants (i.e. phenols or amines), polyols, phosphites, β-diketones, substituted amines and hydrotalcite. NBR rubbers typically utilize stabilizer systems including antioxidants of many classes (phenolic, amines and phosphites). Additional examples include sodium oleate, calcium stearate, zinc stearate, dioctyl phthalate, BHT (butylated hydroxy toluene), ESO (epoxidized soybean oil), and a variety of barium-zinc salt compounds. In some embodiments, each stabilizer may be present in levels of about 0.01 to about 15.0, preferably about 0.5 to about 8.0, more preferably 2.0 to 4.0 parts per hundred parts of polyvinyl chloride resin. The levels of usage of the stabilizer vary by the chemical identity the active ingredient and by the number of stabilizers present in any stabilizer package.

Acrylonitrile Butadiene Rubbers (NBR)

NBR (Acrylonitrile-Butadiene Rubber) may be classified by the International Institute of Synthetic Rubber Producers (IISRP). NBR is comprised of unsaturated copolymers of 2-propenenitrile and various butadiene monomers (1,2-butadiene and 1,3-butadiene). In some instances, these elastomers contain acrylonitrile to butadiene amounts of about 25 wt % to 50 wt %, 28 wt % to 39 wt % or 30 wt % to 35 wt % acrylonitrile. The disclosure herein pertains to a nitrile polymer blend comprised of acrylonitrile-butadiene copolymer blended with a PVC resin.

Crumb Rubber

The term "Crumb rubber" relates to a rubber material derived by reducing scrap tire or other rubber into uniform granules with the inherently reinforcing materials, such as steel and fiber removed along with any other type of inert contaminants such as dust, glass, or rocks. The crumb rubber can include particles of reclaimed rubber. Reclaimed rubber can be recycled rubber, which can be derived from synthetic and/or natural rubbers or plastics. In embodiments, the crumb rubber can be made of 100 percent recycled tires. At least a portion of the particles of reclaimed rubber can be passed through a series of mesh sieves before the crumb rubber is incorporated into the rubber composition. For example, from 10 percent to 50 percent of the particles of reclaimed rubber can be passed through a 30 to 100 mesh or other mesh sieve.

Biofouling Agents

The main sources of fouling in a given water body can be the result of sediments (i.e., scale, silt, algae and sludge), corrosion and bacterial activity. Lack of knowledge of aeration systems and equipment, taxonomy and ecology of tropical fouling organisms is a major stumbling block to development of effective systems for antifouling management.

Chemical fouling inhibitors can reduce fouling in many systems, mainly by interfering with the crystallization, attachment, or consolidation steps of the fouling process. Examples for water systems are: chelating agents, such as EDTA, long-chain aliphatic amines or polyamines, such as octadecylamine, helamin, and other suitable amines, organic phosphonic acids, such as etidronic acid, or polyelectrolytes, such as polyacrylic acid and polymethacrylic acid.

Non-toxic anti-fouling coatings or embedded components are hydrophilic coatings. These coatings or embedded components rely on hydration whereby the substitution of water for proteins and microorganisms is minimized. Some examples without limiting the disclosure herein are coatings based on hydrated zwitterions, such as glycine betaine and sulfobetaine. These coatings or embedded components prevent bacteria attachment and biofilm formation.

The ability of carbon nanotubes (CNTs) to undergo surface modification allows them to form nanocomposites (NCs) with materials such as polymers, metal nanoparticles, biomolecules and metal oxides. The biocidal nature, protein fouling resistance, and fouling release properties of CNT-NCs render them the perfect material for biofouling prevention.

The disclosure herein employs at least one biofouling agent is selected from the group consisting of glycine betaine, sulfobetaine, titanium dioxide nanotubes or combinations thereof, wherein the biofouling agent is mixed with the self-sinking PVC tubing compositions described herein. Therefore, the biofouling agent is embedded at the surface of the tubing after further compounding using melt extrusion whereby the composition is formed into any desired shape (i.e., tubing).

Furthermore, fouling can be reduced by maintaining a relatively high fluid velocity throughout the aeration tubing.

Compounding

During the compounding process the PVC resin is combined with a other components, including heat stabilizers, lubricants and plasticizers. Additional additives may include fillers, antioxidants, etc. Additives may influence or determine mechanical properties, UV light and thermal stability, etc. In the compounding process, the additives are mixed with the PVC resin. In one embodiment, the compounding method employs a high-speed mixer that thoroughly blends all the components. The result is a semi-dry to dry powder, which may be fed into processing equipment.

The blends obtained from the mixing process can be further compounded with a mixer such as a Banbury batch mixer, a Farrel Continuous Mixer or a single or twin screw extruder. In some embodiments, the semi-dry to dry blend may be mixed using a Brabender mixer, a Henschel mixer or a ribbon blender. In some embodiments, the semi-dry to dry blend may be further compounded using melt extrusion and formed into any desired shape (i.e., pellet, tubing, etc.).

Examples 1A-1E (PVC Hose Compositions and Hose Portion Examples)

The powdered PVC/VA (polyvinyl chloride/polyvinyl acetate copolymer, ethyl-vinyl acetate copolymer were placed in a high intensity 500 L Henschel dry powder mixer along with the stabilizers. The PVC/VA and stabilizers calcium stearate and zinc stearate were mixed with sufficient shear to raise the temperature of the coated PVC to at least about 80° C.

Then, the TOTM (Tris-2-Ethylhexyl-Trimellitate) and DOA (di-octyl adipate) were added to the PVC/VA in the mixer and the temperature lowers for about 5 minutes from about 80° C. to about 60° C. During this time the TOTM and DOA are absorbed the mixture forms a dry to wet powder.

After about 8 to 10 minutes the NBR rubber and meshed tire were blended with the PVC/VA as well as the remaining components including the filler, stearic acid, antioxidant (ADK STAB AO-50) and biofouling agents (glycine betaine, sulfobetaine, titanium dioxide nanotubes). Then, the mixture was intimately blended and after about 5 minutes the temperature lowers to about 40° C. At this time, the mixture was added to a 1000 L cooler mixer and the mixture was allowed to cool to room temperature.

The mixture was transferred from the cooler mixture and fluxed through an extruder with a first zone temperature of about 175° C., a second/third zone temperature of 145° C. and a fourth zone temperature of 120° C. to yield blends showing good physical properties. During extrusion the blend is passed through a die with a blade that cuts the pelletized material to form pellets with a diameter of about 5 mm and a length of about 3 mm. The, a cooling system cools the pellets from about 125° C. to room temperature. Table 1 shows the components and relative parts-per-hundred amounts used to prepare Examples 1A-1E.

hose portions of Table 2 with the amount and type of filler and the inner diameter and outer diameter of the tube are selected to have a specific gravity suitable for a surface water aeration of a body of water with a large surface area at a depth of about 20 m and a length of about 10 km or less.

TABLE 2

| Formulation | Copper Dioxide (Parts-per-Hundred Resin) | I.D. mm | O.D. mm |
| --- | --- | --- | --- |
| 1A | 116.16 | 10 | 17.5 |
| 1B | 83.87 | 12.7 | 24.2 |
| 1C | 128 | 15.9 | 27.1 |
| 1D | 130.3 | 19.1 | 32.4 |
| 1E | 132.44 | 25.4 | 42.9 |

Properties and Applications

The compositions disclosed herein are useful to produce highly environmentally resistant yet flexible plastic hose portion aeration tubing that is self-sinking, non-kinking and holds no memory when deployed. The self-sinking property of the tubing is attributed to the composition disclosed herein and in particular, the amount and type of filler are predetermined depending on the inner diameter and outer diameter of the tube, the depth of the body of water and the type of application site (i.e., fish farm, harbor and an environmental treatment facility, etc.).

For example, at a fish or shrimp farming application site the depth may be about 2 m to 3 m to the bottom of the body

TABLE 1

Formulations 1A-1E

| Components | Description | PHR (Parts-per-Hundred Resin) | | | | |
| --- | --- | --- | --- | --- | --- | --- |
| | | 1A | 1B | 1C | 1D | 1E |
| NBR | Buna-N,Perbunan,acrylonitrile butadiene rubber | 15 | 15 | 15 | 15 | 15 |
| CRUMBED TIRE | 30-100 Mesh | 65 | 65 | 65 | 65 | 65 |
| PVC/VA | PVC/VA Copolymer resins, Inherent viscosity = 0.787, K-value = 60.9 | 100 | 100 | 100 | 100 | 100 |
| EVA742 | Ethylene-vinyl acetate | 25 | 25 | 25 | 25 | 25 |
| DOA | Di-octyl adipate low temperature plasticizer | 35 | 50 | 50 | 50 | 50 |
| TOTM | Tris-2-Ethylhexyl-Trimellitate | 50 | 50 | 50 | 50 | 50 |
| Copper Dioxide | Filler | 116.16 | 83.87 | 128 | 130.3 | 132.44 |
| Calcium stearate | Heat stabilizer | 3 | 3 | 3 | 3 | 3 |
| Zinc stearate | Heat stabilizer | 3 | 3 | 3 | 3 | 3 |
| stearic acid | Internal Lubricant | 0.03 | 0.03 | 0.03 | 0.03 | 0.03 |
| ADK STAB AO-50 | Antioxidant | 0.025 | 0.025 | 0.025 | 0.025 | 0.025 |
| Glycine betaine | Biofouling agent | 0.025 | 0.025 | 0.025 | 0.025 | 0.025 |
| Sulfobetaine | Biofouling agent | 0.025 | 0.025 | 0.025 | 0.025 | 0.025 |
| TNT (titanium nanotube) | Biofouling agent | 0.05 | 0.05 | 0.05 | 0.05 | 0.05 |

Hose Portion Examples:

In some embodiments, the hose portions derived from Formulations 1A-1E of Table 1 are used with a suitable amount of filler to produce the hose portions with the I.D.'s and O.D.'s reported with Table 2. In some embodiments, the of water. In some embodiments, the amount and type of filler and the inner diameter and outer diameter of the tube are selected to have a specific gravity suitable for a surface water and/or environmental treatment at a depth of about 5 m. In some embodiments, the amount and type of filler and the inner diameter and outer diameter of the tube are selected to have a specific gravity suitable for deicing of a lake or pond at a depth of about 15 m. In some embodiments, the amount and type of filler and the inner diameter and outer diameter of the tube are selected to have a specific gravity suitable for a surface water aeration of a body of water with a large surface area at a depth of about 20 m and a length of about 10 km or less. In some embodiments, the amount and type of filler and the inner diameter and outer diameter of the tube are selected to have a specific gravity suitable for agitation to create a bubble curtain and/or bubble barrier in a harbor at a depth of about 100 m. Therefore, as the outer diameter increases the volume of the tube and the wall thickness both increase. As such, the addition of more or less filler with the disclosed compositions is needed to produce a tube with the desired specific gravity, which enables the tube to sink to an appropriate depth at a specific application site.

The aeration system is manufactured to deliver air into a body of water such as a pond, lagoon or lake bed from a solar, wind or electric powered aerator. The rising air bubbles from the aeration system provides life-giving oxygen to the water and creates an essential circulation pattern. The result is healthier fish, reduced algae growth, fewer dissolved toxic gasses, and less odor and elimination of stagnation. The aeration hose is constructed of heavy, negative-buoyancy, plastic material, which allows it to descend to the bottom of the pond, lagoon or lake without the use of extra weights. The non-clogging performance of the apertures of the first and second protective layers provides uniform air pressure distribution inside the hose. Designed for even distribution of air bubbles along the entire hose for any length. In some embodiments, one or more 75 Watt air pump or compressor can supply 1000 meters of aeration hose disclosed herein.

There is no restriction on the length of the tube, and the tubing can be manufactured to cover a very large surface area. Compressed air enters the tubing creating an inner pressure along both sides of the entire length of tubing and allows the compressed air to release through a porous surface in the tubing, creating efficient micro-bubbles that prevent clogging and fowling, along the entire length of the tubing. The released air from the porous surface forms a bubble curtain of uniform and evenly dispersed fine bubbles that optimize the oxygen transfer, and lift water which aids in complete circulation throughout the water column surrounding the tube. The size of the bubble matters greatly for the applications disclosed herein, whereby fine bubbles (micro bubbles) are important for achieving exacting results whether oxygenating a wastewater treatment plant, using aeration to biologically remove excess nutrients, using aeration for liquid mixing, deicing and even air bubble curtain applications.

During operation the compressed air enters the aeration hose creating an inner pressure. Thousands of precision perforations around the entire length of the hose allow compressed air to release through the perforations at a certain pressure. This creates efficient micro-bubbles that prevent clogging and fowling (typically found in porous diffusers), along the entire length of the aeration hose. The released air from the holes forms a bubble curtain of uniform and evenly dispersed fine bubbles, which optimizes oxygen transfer and lifts water which aids in complete circulation throughout the water column. The aeration hose disclosed herein (Smart Aeration Hose®) functions without moving parts or electricity in the water, it increases performance efficiency while significantly reducing electrical and maintenance costs in comparison to other aeration systems. For deicing purposes, the bubbles leaving the Smart Hose® also bring dense, heavier, warmer water from the depths to the surface, inhibiting ice formation.

Since the tubing operates without moving parts or electrical components in the body of water at the application sire, the performance and efficiency is improved and with significantly reduced electrical and maintenance related costs in comparison to other aeration systems.

For deicing purposes, the air bubbles leaving the tubing also bring dense, heavier, warmer water from the depths of the body of water to the surface, which results in efficient inhibition of ice formation.

Additional properties derived from tubing manufactured from the disclosed compositions include but are not limited to strong physical properties such as high tensile strength, modulus and elongation; water proof and/or hydrophobic when the tubing is not in operation; flexible and is easy to install and is safe for the environment (i.e., does not contain lead); high oxygen transfer rate; highly resistant plastic material (i.e., chemicals, salinity, temperature).

In some embodiments, the tubing derived from the disclosed compositions has applications ranging from farm ponds and industrial projects and is suitable for fresh and salt water applications in shallow and deep bodies of water. Other applications include but are limited to commercial, government and private applications; aeration sewage lagoons; wastewater treatment process plants; leachate ponds; earthen ponds, dugouts and lakes, etc.; waterways and channels; storm water retention ponds; septic systems; aquaculture; deicing docks, power plant water intake, marina slips, shoreline and/or water retention structures, industrial ship docking, ocean freight & Maritime transport, pumping operations and nuclear power generating plants; efficient bottom-to-top water circulation and mixing for water treatment, deicing, and other related applications; pathogen reduction, whereby the bubbles lift deeper waters to the surface for UV exposure.

In some embodiments, the tubing derived from the disclosed compositions has applications ranging from underwater air bubble curtains for protecting fish and marine mammals from underwater blasting and pile driving noise; protecting marine mammals from offshore oil platforms and wind power farm construction and continuous operation vibrations and noises (i.e., machinery and engine noise); containing oil spills in a body of water within a selected area; controlling the movement of marine life, plants and debris. In some aspects, a bubble curtain and/or bubble barrier can control the movement of marine life and floating debris and control the migration of jellyfish, fish, seagrass, debris, sediments, etc. This may provide an improvement in water quality, including but not limited to improved water clarity, reduction of algae and reduced $H_2S$ and odor suppression.

Definitions

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained. It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. As used herein, the term "comprising" means including elements or steps that are identified following that term, but any such elements or steps are not exhaustive, and an embodiment can include other elements or steps.

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

What is claimed is:

1. An aeration hose capable of diffusing bubbles of air within a body of water, comprising:
   a) a hose portion derived from a composition, comprising a polyvinyl chloride resin; a first rubber component; a second rubber component; at least one copolymer; at least one low temperature plasticizer; at least one filler comprising copper dioxide; at least one heat stabilizer; at least one internal lubricant; at least one antioxidant; and at least one biofouling agent, wherein the hose portion comprises an outer hose portion, an inner hose portion and a plurality of hose apertures capable of receiving and diffusing pressurized air, wherein the hose is flexible and has no memory, and wherein the hose apertures are provided therethrough the inner hose portion and the outer hose portion and proportionally spaced about the outer hose portion along a length of the hose portion;
   b) a first protective layer portion surrounding an outer diameter of the hose portion, comprising a plurality of first protective layer apertures provided therethrough an inner protective sheath diameter and an outer protective sheath diameter and spaced along a length of the protective sheath, wherein the first protective layer is flexible and has memory; and
   c) a second protective layer portion surrounding an outer diameter of the first protective layer portion, comprising a plurality of second protective layer apertures provided therethrough an inner second protective layer diameter and an outer second protective layer diameter and spaced along a length of the second protective layer, wherein the second protective layer is flexible and has memory,
   wherein the second protective layer apertures are capable of providing communication for the air to flow to a body of water from the corresponding first protective layer apertures, and wherein the hose apertures are capable of providing communication for the air to flow from the inner hose portion to a plurality of corresponding first protective layer apertures.

2. The aeration hose of claim 1, wherein the hose apertures are comprised of between about 20 to 500 apertures per square inch of the hose portion.

3. The aeration hose of claim 1, wherein the first protective layer apertures are comprised of between about 20 to 500 apertures per square inch of the first protective layer.

4. The aeration hose of claim 1, wherein the second protective layer apertures are comprised of between about 20 to 500 apertures per square inch of the second protective layer.

5. The aeration hose of claim 1, wherein the hose apertures, first protective layer apertures and second protective layer apertures each independently have an aperture diameter of between about 0.05 mm and 3 mm.

6. The aeration hose of claim 1, wherein the first protective layer is comprised of polyurethane, silicon, EPDM (ethylene propylene diene monomer), thermoplastic rubber or natural rubber.

7. The aeration hose of claim 1, wherein the second protective layer is comprised of silicone rubber, silicon, EPDM (ethylene propylene diene monomer), thermoplastic rubber or natural rubber.

8. The aeration hose of claim 1, wherein the first protective layer is bonded to the outer surface of the hose portion along length of the hose portion.

9. The aeration hose of claim 1, wherein the second protective layer is bonded to the outer surface of the first protective layer along length of the first protective layer.

10. The aeration hose of claim 1, wherein the aeration hose is comprised of negative buoyancy plastic.

11. The aeration hose of claim 1, wherein the hose portion is comprised of negative buoyancy plastic.

12. The aeration hose of claim 1, wherein the aeration hose is comprised of negative buoyancy plastic, and wherein the aeration hose is deployed the bottom of the body of water without weights.

13. The aeration hose of claim 1, wherein the hose portion is comprised of negative buoyancy plastic, and wherein the aeration hose is deployed the bottom of the body of water without weights.

14. The aeration hose of claim 1, wherein the hose portion has an inner diameter of between about 0.1 inches and 3 inches and an outer diameter of between about 0.23 inches and 5 inches.

15. The aeration hose of claim 1, wherein the hose portion has an inner diameter of about 0.38 inches, 0.5 inches, 0.63 inches, 0.75 inches or 1.0 inch.

16. The aeration hose of claim 1, wherein the hose portion has an outer diameter of about 0.69 inches, 0.96 inches, 1.065 inches, 1.275 inches or 1.69 inches.

17. The aeration hose of claim 1, wherein the hose portion is capable of diffusing bubbles of air in a body of water that is at a temperature between about −10° C. and 70° C.

18. The aeration hose of claim 1, wherein the first protective layer is comprised of tear resist polyurethane with a thickness of between about 0.1 mm to 5 mm.

19. The aeration hose of claim 1, wherein the second protective layer is comprised of heat resist silicone rubber with a thickness of between about 0.1 mm to 5 mm.

20. A method of aerating and/or deicing a body of water with an aeration hose capable of diffusing bubbles of air within a body of water, comprising: a) a hose portion derived from a composition, comprising a polyvinyl chloride resin; a first rubber component; a second rubber component; at least one copolymer; at least one low temperature plasticizer; at least one filler comprising calcium carbonate; at least one heat stabilizer; at least one internal lubricant; at least one antioxidant; and at least one biofouling agent, wherein the hose portion comprises an outer hose portion, an inner hose portion and a plurality of hose apertures capable of receiving and diffusing pressurized air, wherein the hose is flexible and has no memory, and wherein the hose apertures are provided therethrough the inner hose portion and the outer hose portion and proportionally spaced about the outer hose portion along a length of the hose portion; b) a first protective layer portion surrounding an outer diameter of the hose portion, comprising a plurality of first protective layer apertures provided therethrough an inner protective sheath diameter and an outer protective sheath diameter and spaced along a length of the protective sheath, wherein the first protective layer is flexible and has memory; and c) a second protective layer portion surrounding an outer diameter of the first protective layer portion, comprising a plurality of second protective layer apertures provided therethrough an inner second protective layer diameter and an outer second protective layer diameter and spaced along a length of the second protective layer, wherein the second protective layer is flexible and has memory, wherein the second protective layer apertures are capable of providing communication for the air to flow to a body of water from the corresponding first protective layer apertures, and wherein the hose apertures are capable of providing communication for the air to flow from the inner hose portion to a plurality of corresponding first protective layer apertures.

* * * * *